US012343332B2

(12) United States Patent
Berdzik-Kalarus et al.

(10) Patent No.: US 12,343,332 B2
(45) Date of Patent: *Jul. 1, 2025

(54) TREATMENT OF A BACTERIAL VAGINAL INFECTION

(71) Applicant: Adamed Pharma S.A., Czosnow (PL)

(72) Inventors: Sylwia Berdzik-Kalarus, Katowice (PL); Daniel Sulikowski, Warsaw (PL)

(73) Assignee: ADAMED PHARMA S.A., Czosnow (PL)

( * ) Notice: Subject to any disclaimer, the term of this patent is extended or adjusted under 35 U.S.C. 154(b) by 0 days.

This patent is subject to a terminal disclaimer.

(21) Appl. No.: 18/313,671

(22) Filed: May 8, 2023

(65) Prior Publication Data

US 2023/0270725 A1 Aug. 31, 2023

Related U.S. Application Data

(62) Division of application No. 16/604,850, filed as application No. PCT/EP2018/058508 on Apr. 3, 2018, now Pat. No. 11,684,608.

(30) Foreign Application Priority Data

Apr. 14, 2017 (EP) ..................................... 17461524

(51) Int. Cl.
| | | |
|---|---|---|
| *A61K 31/4178* | (2006.01) | |
| *A61K 9/00* | (2006.01) | |
| *A61K 9/06* | (2006.01) | |
| *A61K 9/20* | (2006.01) | |
| *A61K 31/4164* | (2006.01) | |
| *A61K 31/7048* | (2006.01) | |
| *A61P 15/02* | (2006.01) | |
| *A61P 31/04* | (2006.01) | |

(52) U.S. Cl.
CPC ........ *A61K 31/4178* (2013.01); *A61K 9/0034* (2013.01); *A61K 9/06* (2013.01); *A61K 9/2018* (2013.01); *A61K 31/4164* (2013.01); *A61K 31/7048* (2013.01); *A61P 15/02* (2018.01); *A61P 31/04* (2018.01)

(58) Field of Classification Search
None
See application file for complete search history.

(56) References Cited

U.S. PATENT DOCUMENTS 11,684,608 B2 * 6/2023 Berdzik-Kalarus ..... A61P 15/02
514/31
2020/0078337 A1 3/2020 Berdzik-Kalarus et al.

FOREIGN PATENT DOCUMENTS

WO WO-2011122978 A1 * 10/2011 ........... A61K 31/422
WO WO 2018/188992 A1 10/2018

OTHER PUBLICATIONS

ChEBI: 131714—furagin, Feb. 22, 2017 (Year: 2017).*
Donders et al., "Treatment of bacterial vaginosis: what we have and what we miss" Expert Opinion on Pharmacotherapy vol. 15 No. 5 pp. 645-657, DOI: 10.1517/14656566.2014.881800 (Year: 2014).*
English machine translation of WO2011/122978, downloaded from patents.google.com (Year: 2011).*
Polatti, "Bacterial Vaginosis, Atopobium vaginae and Nifuratel" Current Clinical Pharmacology vol. 7 pp. 36-40 (Year: 2012).*
Czeizel, A. E. et al., "Population-based case-control teratologic study of furazidine, a nirofuran-derivative treatment during pregnancy," Clinical Nephrology, Dustri Verlag, Nuenchen-Deisenhofen, DE, vol. 53, No. 4, Jan. 1, 2000, pp. 257-263.
De Backer, E. et al., "Antibiotic susceptibility of Atopobium vaginae," BMC Infectious Disease, Biomed Central, London, GB, vol. 6, No. 1, Mar. 16, 2006.
Donders, G. "Diagnosis and management of bacterial vaginosis and other types of abnormal vaginal bacterial flora: A review," Obsterical and Gynecological Sur, vol. 65, No. 7, Jan. 1, 2010.
International Preliminary Report on Patentability including Written Opinion of the International Searching Authority issued Oct. 15, 2019 in connection with PCT International Application No. PCT/EP2018/058508.
International Search Report issued Jun. 15, 2018 in connection with PCT International Application No. PCT/EP2018/058508.
Kuchuma, Z. N. Action of furagin, nystatin and Levorin with bile acids on the vagnial microflora of pregnant women, Vrachebnoe Delo, Oct. 1986.
Tsyganenko, A. Y. et al. Using cluster analysis for evaluation of sensitivity to antibiotics of pathogens isolated from women with genital inflammatory disease, Mikrobiolohichny, Akademija Nauk Urainy, Institut Mikrobiolohii I Virusolohii Im. Akad. D. K. Zabalotnoho, Ukraine, vol. 69, No. 4.
Written Opinion issued Jun. 15, 2018 in connection with PCT International Application No. PCT/EP2018/058508.

\* cited by examiner

*Primary Examiner* — Eric Olson
(74) *Attorney, Agent, or Firm* — Gary J. Gershik

(57) ABSTRACT

The present invention relates to furazidin for vaginal use in the treatment of a bacterial vaginal infection. Preferably, the bacterial vaginal infection is caused by *Gardnerella vaginalis* and/or *Atopobium vaginae* bacteria.

20 Claims, No Drawings

TREATMENT OF A BACTERIAL VAGINAL INFECTION

CROSS-REFERENCE TO RELATED APPLICATIONS

This application is a divisional of U.S application Ser. No. 16/604,850, filed Oct. 11, 2019, which is a § 371 national stage of PCT International Application No. PCT/EP2018/058508, filed Apr. 3, 2018, claiming priority of European Patent Application No. 17461524.5, filed Apr. 14, 2017, the contents of each of which are hereby incorporated by reference in their entirety.

The present invention relates to the field of medicine. In particular, the present invention relates to use of furazidin to treat of bacterial infections of the vagina.

Bacterial vaginosis (bacterial vaginal infection), and bacterial vaginitis is most often caused by a bacterial infection or has a mixed etiology (bacterial+fungal and/or protozoal infection). The infection results from an abnormal growth of bacteria of the *Lactobacillus* spp. strain on the surface of the vaginal epithelium and the qualitative change in a composition of the bacteria of the vagina. Bacteria from the *Lactobacillus* spp. strain, due to a strong adhesion to the vaginal epithelium and their ability to produce the lactic acid protect the environment of the vagina against bacterial and fungal infections. In the majority of cases, bacterial vaginosis and mixed infections of the vagina are caused by the anaerobic bacteria *Gardnerella vaginalis* and *Atopobium vaginae*. Interestingly, in more than 90% of cases, a biofilm formed on the epithelial cells of the vagina of women with bacterial vaginoses, was composed of both *Gardnerella vaginalis*, and *Atopobium vaginae*.

Change of qualitative composition of bacterial of the vagina may be due to several factors: improper hygiene, decreased level of estrogens (as a result of hormone replacement therapy), diabetes, acquired immunodeficiency syndrome, treatment with antibiotics, treatment with immunosuppressive drugs, cancer treatments and as a result of anemia.

The treatment of vaginal infections and inflammations of bacterial and mixed origin caused by the bacterium *Gardnerella vaginalis*, and *Atopobium vaginae* is based on oral administration of metronidazole (500 mg 2×daily for 7 days or as a single dose of 2 g). It is also possible to use clindamycin orally (300 mg 2×daily for 7 days), clindamycin 2% vaginal cream applied once daily (at night) for 7 days or metronidazole 0.75% vaginal gel administrated once daily (at night) for 5 days.

However, the use of these preparations is often accompanied with several side effects, typically occurring during antibiotic therapy. In addition, the standard oral and/or vaginal clindamycin and/or metronidazole treatment is associated with an increased risk of recurrence of infections and inflammation, counting even up to 30% of cases. This results from the disturbance of the vaginal flora in consequence of the negative effect on the *Lactobacillus* spp. growth.

In the treatment of vaginal infections, it is also known to use a vaginal ointment comprising nifuratel. The advantage of using nifuratel is its high activity against *Gardnerella vaginalis*, and *Atopobium vaginae*. Nifuratel is generally well-tolerated, but its activity is less than that, for example, against *Gardnerella vaginalis* for clindamycin.

Therefore, it is desirable to provide compounds with preferential inhibition of *Gardnerella vaginalis* and *Atopobium vaginae* bacterial growth with possible concurrent minimal impact on the *Lactobacillus* spp. activity, which are suitable for use in the treatment of bacterial vaginosis.

The present inventors have surprisingly found that furazidin displays a very high activity against *Gardnerella vaginalis* and *Atopobium vaginae*, which is comparable to that for clindamycin. At the same time, furazidin does not cause a depletion of the natural flora of *Lactobacillus* spp. as much as clindamycin.

Furazidin (Furagin, 1-[3-(5-nitro-2-furyl)-2-propenylideneamino-imidazolidine-2,4-dione) is an old drug used primarily in infections caused by *Staphylococcus, Streptococcus*, and anaerobic bacteria. Due to the ability to accumulate in the urine, furazidin has been used in the oral treatment of acute and chronic urinary tract infections, prostate infections, recurrent urinary tract infections, after surgery of the urinary tract, and prostate inflammation. So far, the vaginal use of furazidin remains unknown.

Tsyganenko A. et al. in "Use of methods of cluster analysis for sensitivity to antibiotics evaluation sensitivity to antibiotics of causative agents of inflammatory diseases in internal female genital organs" Mikrobiolohichny, Akademija Nauk Ukrainy, Instytut Mikrobiolohii i Virusolohii, Im. Akad., D. K. Zabalotnoho, Ukraine, vol. 69 no. 4, p. 45 reported sensitivity of some agents in women's genital inflammatory diseases. The document is, however, silent about vaginal use of the agents. Furthermore, it discloses furazidin activity neither on *Gardnerella vaginalis* nor on *Atopobium vaginae*.

Furthermore, Kuchma Z. M in "[Action of furagin, nystatin and levorin with bile acids on the vaginal microflora of pregant women]." Vrachebnoe Delo October 1986, no. 10 p. 10-13 mentions that some bile acids potentiate the effect furazidin (furagin) on staphylococci and escherichae. This document does not report a vaginal use of furazidin, and also is silent about treatment of bacterial vaginosis with furazidin alone or with a combination of furazidin and bile acids.

Accordingly, the present invention relates to a vaginal use of furazidin for the treatment of bacterial vaginal infection.

The term "vaginal use of furazidin for the treatment of bacterial vaginal infection" means that furazidin is to be applied inside the vagina. The term "vaginal use" is to be understand as "intravaginal use".

In one embodiment, bacterial vaginal infection is caused by *Gardnerella vaginalis*, and in another embodiment, bacterial vaginal infection is caused by *Atopobium vaginae*. In further embodiment, bacterial vaginal infection is caused by *Gardnerella vaginalis* or by *Atopobium vaginae*.

In a further embodiment, bacterial vaginal infection is of a mixed type. Preferably, in one embodiment, the mixed type bacterial vaginal infection is caused by both *Gardnerella vaginalis*, and *Atopobium vaginae*. It should be emphasized that *Gardnerella vaginalis* and *Atopobium vaginae* are the most common cause of bacterial vaginal infections.

In one preferable embodiment, the vaginal bacterial infection is a recurrent vaginal bacterial infection.

Bradshaw, C. S. et al. in The Journal of Infectious Diseases, Vol. 194, Issue 6, 15 Sep. 2006, p. 828-836 reported that *G. vaginalis* was detected in 100% and *A. vaginae* in 75% of women with recurrent bacterial vaginitis. Accordingly, use of furazidin in such cases of recurrent bacterial infections is especially advantageous.

Therefore, in one embodiment the recurrent bacterial vaginal infection is caused by *G. vaginalis*. In another embodiment the recurrent bacterial vaginal infection is caused by *A. vaginae*. In further another embodiment, the recurrent bacterial vaginal infection is caused by *G. vaginalis* and *A. vaginae*. Preferably, the recurrent bacterial vaginal infection is caused by *G. vaginalis*, more preferably by *G. vaginalis* and *A. vaginae*.

The term 'recurrent infection' means that the infection occurs again or repeatedly after previous treatment such as for example with metronidazol (such as orally) or clindamycin (such as orally or vaginally).

In yet another embodiment, the vaginal bacterial infection is accompanied by a fungal infection. This bacterial/fungal mixed type is a very common type of vaginal infection, since a change in a composition of the bacteria of the vagina caused by abnormal growth of *Lactobacillus* spp. strain results also in an uncontrolled and pathologic growth of endogenous *Candida albicans* and/or *Candida glabrata*. Thus, in one embodiment the fungal infection is caused by *Candida albicans*, in another embodiment, the fungal infection is caused by *Candida glabrata*, and in yet another embodiment, the fungal infection is caused by *Candida albicans* and *Candida glabrata*.

Furazidin can be administered in any of the known pharmaceutical compositions used vaginally. Such a pharmaceutical composition will contain, of course, in addition to the active compound, furazidin, vaginally acceptable vehicle.

The pharmaceutical compositions suitable to treat infections caused by the bacteria mentioned above can be in solid, semi-solid or liquid forms, and can take a form of tablets, capsules, ovules, suppositories, or cream, ointment, gel, lotion, foam, solution, suspension, thin film or liposomal composition, to be applied or to put deeply into the vagina, with a content in furazidin from 1 to 1000 mg per single dose, more preferably from 10 to 500 mg per single dose, most preferably from 40 to 300 mg per single dose. The person skilled in the art will be able to select the right dosage depending on the selected preparation. Such preparations may be administered in infected patients according to conventional techniques; according to a preferred embodiment, they are administered on a regular basis, preferably daily.

Pharmaceutical compositions may be prepared according to conventional techniques, and contains pharmaceutically and vaginally acceptable vehicle that can be formed using pharmaceutically and vaginally excipients, adjuvants and/or carriers, and may also contain, in combination, one or more active principles with complementary or, in any case, useful activity. Vaginally acceptable vehicles are vehicles, which can be used for vaginal forms and which are not toxic, not irritating and are readily usable. Guidance on the preparation of such pharmaceutical compositions and their forms can be found in *Farmacja Stosowana. Podrecznik dla studentów farmacji*. Ed. S. Janicki, A. Fiebiga, M. Sznitowska; Ed. IV, Wydawnictwo Lekarskie PZWL, 2008 Warszawa.

The active agents which may be used in combination with furazidin of the present invention include, as mentioned above, but are not limited to, antifungal agents, antibacterial agents, antiseptic agents, pH modifiers, probiotics; such active ingredients may be administered together with furazidin (i.e. they may be for instance contained in the same composition as furazidin) or they may be administered separately from or in temporal proximity with furazidin.

Examples of antifungal agents include 1-hydroxy-2-pyridone compounds and their salts, e.g. ciclopirox, rilopirox, piroctone, ciclopirox olamine; imidazole derivatives and their salts, e.g. clotrimazole, econazole, isoconazole, ketoconazole, miconazole, tioconazole, bifonazole, fenticonazole and oxiconazole; polyene derivatives and their salts, e.g. nystatin, natamycin and amphotericin; allylamine derivatives and their salts, e.g. naphtifine and terbinafine; triazole derivatives and their salts, e.g. fluconazole, itraconazole, terconazole and voriconazole; morpholine derivatives and their salts, e.g. amorolfine and morpholines disclosed in U.S. Pat. No. 5,120,530, herein incorporated by reference; griseofulvin and related compounds, e.g. griseofulvin; undecylenic acid and its salts, in particular, the zinc and calcium salts of undecylenic acid; tolnaphtate and its salts; and flucytosine and its salts.

Examples of antibacterial agents include metronidazole, clindamycin, macrolide antibiotics such as erythromycin, oleandomycin, flurithromycin, azithromycin and claritromycin and salts thereof, beta-lactam antibiotics such as penicillin, ampicillin, amoxicillin and salts thereof, fluoroquinolones such as ofloxacine, norfloxacine, ciprofloxacine and salts thereof, aminoglycosides such as gentamycin, amikacin, kanamycin, neomycin and salts thereof.

Examples of the antiseptic agents include benzalkonium chloride, triclosan, salicylic acid, benzoic acid and their salts, p-hydroxybenzoic acid and its esters.

Examples of pH modifiers include ascorbic acid, acetic acid, lactic acid, and salts thereof.

Examples of probiotics include species of the genus *Lactobacillus*.

As mentioned above, furazidin can be used to treatment of mixed type bacterial vaginal infection.

Thus, in this case, in one embodiment, the pharmaceutical composition comprises preferably an antifungal agent. The studies on antimicrobial activity of furazidin have surprisingly shown a synergy between furazidin and the antifungal agent.

Preferably, the antifungal agent is selected from nystatin, clotrimazole, econazole, miconazole, terconazole, natamycin, and ciclopirox olamine. Those antifungal agent are especially recommended by some guidelines (see *Clinical Practice Guideline for the Management of Candidiasis: 2016 Update by the Infectious Diseases Society of America Clinical Infectious Diseases* 2016; 62(4):c1-50), and are active at relatively low doses. In a particularly preferred embodiment, the antifungal agent is nystatin. The applicant has found that combination of furazidin with nystatin exhibits synergistic effect against all tested bacteria. This will allow to reduce the total dose of furazidin in a pharmaceutical composition in comparison to a pharmaceutical composition comprising furazidin alone to achieve the same efficacy in the treatment of mixed type infections, especially of bacterial and fungal origin, but also mixed bacterial origin (*Gardnerella vaginalis+Atopobium vaginae*). The applicant has also found that furazidin exhibits synergistic effect with nystatin against *Candida glabrata*. It should be emphasized that none of other nitrofurans acts synergistically against *Candida glabrata*. Therefore, again, this creates possibility to reduce the total dose of antifungal agent in the pharmaceutical composition maintaining the same efficacy in the treatment of mixed type infections with *Candida glabrata*.

In another embodiment, the pharmaceutical composition comprises preferably an antibacterial agent. The studies on antimicrobial activity of furazidin have surprisingly shown a synergy between furazidin and the antibacterial agent.

Preferably, the antibacterial agent is selected from metronidazole, clindamycin, macrolide antibiotics such as erythromycin, oleandomycin, flurithromycin, azithromycin and claritromycin and salts thereof, beta-lactam antibiotics such as penicillin, ampicillin, amoxicillin and salts thereof, fluoroquinolones such as ofloxacine, norfloxacine, ciprofloxacine and salts thereof, aminoglycosides such as gentamycin, amikacin, kanamycin, neomycin, and salts thereof. More preferably, the antibacterial agent is selected from metronidazole and clindamycin. In a particularly preferred embodiment, the antibacterial agent is metronidazole. The applicant has found that combination of furazidin with metronidazole exhibits synergy against all bacterial strains as well as all yeast-like fungi tested.

The uses and the pharmaceutical compositions of the present invention will now be more fully described by the following examples.

EXAMPLES

1. Analysis of the Antimicrobial Activity

Analysis of the antimicrobial activity of furazidin, nitrofurantoin, nifuratel, clindamycin metronidazole, and nystatin was performed to determine the minimum concentration which inhibits the growth of microorganisms—minimal inhibitory concentration values (MIC) using the method described below. Strains used in the study were *Gardnerella vaginalis* ATCC 14018, *Atopobium vaginae* ATCC BAA 55, *Candida albicans* ATCC 90028, and *Candida glabrata* ATCC 2001.

A stock solution for all of compounds was 10000 μg/ml, from which 15 serial dilutions were prepared (500 μg/mL, 250 μg/mL, 125 μg/mL, 62.5 μg/mL, 31.25 μg/mL, 15.6 μg/mL, 7.8 μg/mL, and 3.9 μg/mL, 1.95 μg/mL, 0.98 μg/mL, 0.49 μg/mL, 0.24 μg/mL, 0.12 μg/mL, 0.06 μg/mL, and 0.03 μg/mL).

Macro Dilution Method for Bacteria in a Solid Medium

Serial dilution method in a solid medium was carried out to determine the MIC for furazidin, nitrofurantion, nifuratel, clindamycin, metronidazol, and nystatin for the bacteria. To perform the assay, a pure, 48-hour strain reference culture was used, from which a bacterial suspension with a density of 1.0 McFarland in sterile saline was prepared. The suspension was plated onto Schaedler agar medium supplemented with 5% sheep blood (Becton Dickinson) and a test compound at the appropriate concentration. After incubation, the value MIC was read. Colony growth on the plate indicated no activity of the test compound at tested concentration. As the MIC value, the last lowest concentration as taken, at which there was no microbial growth. The incubation conditions used are shown in Table 1.

The synergistic action of the selected compounds was determined using 2-fold lower concentrations of the selected compound than the obtained MIC. Lack of bacterial growth on the plate was interpreted as a synergic action.

TABLE 1

| Incubation conditions for the strains used in the study | | |
|---|---|---|
| Strain | Incubation conditions | Incubation time |
| *Gardnerella vaginalis* ATCC 14018 | microaerophilic, 37° C. | 72 hours |
| *Atopobium vaginae* ATCC BAA 55 | anaerobic, 37° C. | 7 days |

Macro Dilution Method for Yeast-Like Fungi in a Liquid Medium

Liquid medium RPMI 1640 (Sigma-Aldrich) was used for fungi of the species *Candida albicans* ATCC 90028, and *Candida glabrata* ATCC 2001, in which 15 serial dilution were prepared in a range 500 μg/mL-0.03 μg/mL.

From a pure 24-hour culture on Sabouraud solid medium, a fungal suspension having density of 0.5 McFarland in sterile saline. Next, the suspension was diluted, and was introduced into the RPMI 1640 medium yielding final concentrations of fungi 105 CFU/mL. Incubation was carried out for 24 hours in aerobic conditions in 37° C. Colony growth on the plate indicated no activity of the test compound at tested concentration. As the MIC value, the last lowest concentration as taken, at which there was no microbial growth The synergistic action of the selected compounds was determined using 2-fold lower concentrations of the selected compound than the obtained MIC. Lack of fungal growth on the plate was interpreted as a synergic action.

The results are summarized and compared in the following tables.

TABLE 2

| | MIC values for the single compounds | | | | | |
|---|---|---|---|---|---|---|
| | MIC value [mg/L] | | | | | |
| Strain | Furazidin | Nitrofurantion | Nifuratel | Clindamycin | Metronidazol | Nystatin |
| *Gardnerela vaginalis* ATCC 14018 | 0.49 | 0.98 | 1.95 | 1.95 | 250 | 500 |
| *Atopobium vaginae* ATCC BAA 55 | <0.03 | 1.95 | 3.9 | <0.03 | 0.98 | 500 |
| *Candida albicans* ATCC 90028 | 500 | 500 | >500 | ND | 500 | 1.98 |
| *Candida glabrata* ATCC 2001 | 500 | 500 | 500 | ND | 250 | 1.98 |

ND-not determined;

TABLE 3

Synergy of selected nitrofurans with metronidazole and nystatin against strains of Gardnerella vaginalis, Lactobacillus paracasei, Atopobium vaginae, Candida albicans, Candida glabrata ("+" synergy, "–" no synergy)

|  | Test compound (concentration) | Furazidin (0.25 mg/L) | Nitrofurantoin (0.5 mg/L) | Nifuratel (0.98 mg/L) |
|---|---|---|---|---|
| Gardnerella vaginalis ATCC 14018 | Metronidazole (125 mg/L) | + | + | – |
|  | Nystatin (250 mg/L) | + | + | + |

|  | Test compound (concentration) | Furazidin (0.03 mg/L) | Nitrofurantoin (0.98 mg/L) | Nifuratel (1.95 mg/L) |
|---|---|---|---|---|
| Atopobium vaginae ATCC BAA 55 | Metronidazole (0.5 mg/L) | + | + | – |
|  | Nystatin (250 mg/L) | + | + | + |

|  | Test compound (concentration) | Furazidin (250 mg/L) | Nitrofurantoin (250 mg/L) | Nifuratel (250 mg/L) |
|---|---|---|---|---|
| Candida albicans ATCC 90028 | Metronidazole (250 mg/L) | + | + | + |
|  | Nystatin (0.98 mg/L) | – | – | – |

|  | Test compound (concentration) | Furazidin (250 mg/L) | Nitrofurantoin (250 mg/L) | Nifuratel (250 mg/L) |
|---|---|---|---|---|
| Candida glabrata ATCC 2001 | Metronidazole (125 mg/L) | + | + | + |
|  | Nystatin (0.98 mg/L) | + | – | – |

The data presented above clearly shows that
- all of nitrofurans (furazidin, nifuratel, nitrofurantoin), clindamycin and metronidazole exhibit antibacterial activity against *Gardnerella vaginalis* and *Atopobium vaginae*,
- furazidin exhibits the highest antibacterial activity in the group of nitrofuran derivatives against *Gardnerella vaginalis* and *Atopobium vaginae*,
- furazidin exhibits higher antibacterial activity against *Gardnerella vaginalis* than clindamycin ($MIC_{furazidin} < 0.49$ mg/L vs. $MIC_{clindamycin} < 1.95$ mg/L),
- efficacy of furazidin against *Atopobium vaginae* is comparable to that for clindamycin (MIC<0.03 mg/L),
- no activity of nitrofurans were found against yeast-like fungi tested,
- furazidin and nitrofurantoin, in contrast to nifuratel, show synergistic effects with metronidazole against *Gardnerella vaginalis*, and *Atopobium vaginae*,
- all tested nitrofurans show synergistic effects with nystatin on *Gardnerella vaginalis*, and *Atopobium vaginae*,
- all tested nitrofurans show synergistic effects with metronidazole against *Candida albicans*, and *Candida glabrata*,
- only furazidin shows synergistic effects with nystatin against *Candida glabrata*.

2. Formulation Examples a) Vaginal Tablet Formulation i. Vaginal Tablet with Furazidin

| Component | Quantity [mg/tablet] |
|---|---|
| Furazidin | 500 |
| Lactose | 200 |
| Silicon dioxide | 20 |
| Magnesium stearate | 2 |

A mixing vessel is charged with furazidin, lactose, silicon dioxide, and magnesium stearate. After the mixing vessel was closed, the mixture is stirred for 15 minutes. The resulting mixture is compressed into tablets having mass of 722 mg.

ii. Vaginal Tablet with Furazidin and Clotrimazole

| Component | Quantity [mg/tablet] |
|---|---|
| Furazidin | 250 |
| Clotrimazole | 100 |
| Lactose | 200 |
| Silicon dioxide | 20 |
| Magnesium stearate | 2 |

A mixing vessel is charged with furazidin, clotrimazole, lactose, silicon dioxide, and magnesium stearate. After the mixing vessel was closed, the mixture is stirred for 15 minutes. The resulting mixture is compressed into tablets having mass of 572 mg.

b) Cream Formulation

General preparations for a cream formulation comprising furazidin, optionally with nystatin or metronidazole are as follows. The relevant Phases are defined below.

Phase A and Phase B are heated separately to 60° C. Phase B is added to Phase A, and mixed with a mechanical stirrer. Next, the resulting mixture is homogenized for 1 minute per each 200 g of the mixture at 10000 rpm, followed by addition of Phase C, and the combined phases are mixed with a mechanical stirrer until the mixture reaches room temperature. Yellow cream is obtained.

i. Cream with Furazidin

| Component | Quantity [g/100 g of cream] |
|---|---|
| Phase A | |
| Cithrol DPHS(PEG-30 Dipolyhydroxystearate) | 2.0 |
| Arlamol PS15E (PPG-15 Stearyl Ether) | 6.0 |
| Cithrol PG32IS (Polyglyceryl-3 Diisostearate) | 3.0 |
| Crodamol IPM (Isopropyl Myristate) | 8.0 |
| Mineral oil (Paraffinum liquidum) | 10.0 |
| Phase B | |
| Water | To 100.0 |
| MgSO$_4$•7H$_2$O | 0.7 |
| Phase C | |
| Furazidine | 20.0 | ii. Cream with Furazidin and Nystatin

| Component | Quantity [g/100 g of cream] |
|---|---|
| Phase A | |
| Cithrol DPHS(PEG-30 Dipolyhydroxystearate) | 2.0 |
| Arlamol PS15E (PPG-15 Stearyl Ether) | 6.0 |
| Cithrol PG32IS (Polyglyceryl-3 Diisostearate) | 3.0 |
| Crodamol IPM (Isopropyl Myristate) | 8.0 |
| Mineral oil (Paraffinum liquidum) | 10.0 |
| Phase B | |
| Water | To 100.0 |
| MgSO$_4$•7H$_2$O | 0.7 |
| Phase C | |
| Furazidin | 20.0 |
| Nystatin (6 312 000 j.m./g) | 1.28 g (8000000 j.m.) | iii. Cream with Furazidin and Metronidazole

| Component | Quantity [g/100 g of cream] |
|---|---|
| Phase A | |
| Cithrol DPHS(PEG-30 Dipolyhydroxystearate) | 2.0 |
| Arlamol PS15E (PPG-15 Stearyl Ether) | 6.0 |
| Cithrol PG32IS (Polyglyceryl-3 Diisostearate) | 3.0 |
| Crodamol IPM (Isopropyl Myristate) | 8.0 |
| Mineral oil (Paraffinum liquidum) | 10.0 |
| Phase B | |
| Water | To 100.0 |
| MgSO$_4$•7H$_2$O | 0.7 |
| Phase C | |
| Furazidin | 20.0 |
| Metronidazole | 1.0 | c) Vaginal Globules

General preparation for vaginal globules comprising furazidin, optionally with nystatin. The relevant Phases are defined below.

Phase A is melted, and Phase B is added. After homogenization, globules having 3 grams are formed.

i. Globules with Furazidin

| | Globule 1 | | Globule 2 | |
|---|---|---|---|---|
| Component | Quantity [mg/globule] | Component | Quantity [mg/globule] |
| Phase A | | | Phase A | |
| Cocoa butter | To 3000.0 | Cocoa butter | To 1000.0 |
| Phase B | | | Phase B | |
| Furazidin | 300.0 | Furazidin | 40.0 | ii. Globules with Furazidin and Nystatin

| Globule 3 | | Globule 4 | |
|---|---|---|---|
| Component | Quantity [mg/globule] | Component | Quantity [mg/globule] |
| Phase A | | Phase A | |
| Cocoa butter | To 3000.0 | Cocoa butter | To 1000.0 |
| Phase B | | Phase B | |
| Furazidin | 300.0 | Furazidin | 40.0 |
| Nystatin | 38.4 | Nystatin | 15.8 |
| (6 312 000 j.m./g) | (8 000 000 j.m.) | (6 312 000 j.m./g) | (100 000 j.m.) |

3. Observation of In Vivo Efficacy

Further, in vivo efficacy of furazidin in treatment of bacterial vaginal infections was studied.

A group of 29 women with symptoms of bacterial vaginal infection (abnormal vaginal discharge of characteristic fish-like smell, presence of clue cells, and in several cases itching and/or pain during urination) was screened using PCR techniques for the presence of *Gardnerella vaginalis*, and/or *Atopobium vaginae* as predominant causatives of bacterial vaginal infections. The selection was conducted as described in Kusters J. G. et al., *Eur J Clin Microbial Infect Dis.* 2015; 34(9): 1779-1785. In 26 out of 29 women presence of *Gardnerella vaginalis* or *Atopobium vaginae* or both causatives was conformed. This selected group of 26 women was further screened as to the presence of accompanying *Candida albicans* infection. The selection was performed using method described for example in Trama J. P. et al., *Infect Dis Obstet Gynecol.*, June 2005; 13(2): 63-67 and additionally confirmed by commercial kit *Candida albicans* TaqMan PCR Kit (form Norgenbiotek).

The group was divided into 6 subgroups as follows:

| Group | Causative | No. of patients |
|---|---|---|
| 1 | GV | 3 |
| 2 | AV | 4 |
| 3 | GV + AV | 11 |
| 4 | GV + CA | 1 |
| 5 | AV + CA | 2 |
| 6 | GV + AV + CA | 5 |

GV: *Gardnerella vaginalis*
AV: *Atopobium vaginae*
CA: *Candida albicans*

Five patients in Group 3, one patient in Group 4 and two patients in Group 6 reported previous treatment of bacterial vaginal infections with metronidazole and/or clindamycin.

Patients in Group 1 to Group 3 received intravaginally Globule 2. Patients in Group 4 to 6 received intravaginally Globule 4 (with nystatin), all Groups following the dosing regimen: one globule daily for 10 days. The globules were deposited high in the vagina.

In the Group 6, 3 out of 15 patients was receiving Globule 2 for the first 3 days, but due to lack of improvement, further treatment with Globule 2 was discontinued and Globule 4 was instead administered for further 7 days. Change of this regimen didn't cause change in the amount of administered furazidin comparing to Globule 2 but additionally nystatin was provided to control *Candida* growth.

After 10 days of treatment, all patients showed no symptoms of bacterial vaginal infection such as abnormal vaginal discharge of characteristic fish-like smell, and presence of clue cells. None of the patients reported itching or pain, including pain during urination. Those patients were deemed to be cured and the patients reported improvement of general quality of life. PCR analysis for *Gardnerella vaginalis*, and/or *Atopobium vaginae* showed lack of this bacteria in samples obtained from patients two days after the described treatment had been completed.

The invention claimed is:

1. A method of treating a vaginal bacterial infection in an infected woman comprising vaginally administering 1 mg to 300 mg per day of furazidin to the infected woman to thereby treat the vaginal bacterial infection, wherein the vaginal bacterial infection is caused by *Gardnerella vaginalis* or *Atopobium vaginae* or a combination of the two.

2. The method according to claim 1, wherein the vaginal bacterial infection is caused by *Gardnerella vaginalis*.

3. The method according to claim 1, wherein the vaginal bacterial infection is caused by *Atopobium vaginae*.

4. The method according to claim 1, wherein the vaginal bacterial infection is a mixed type vaginal bacterial infection.

5. The method according to claim 4, wherein the mixed type vaginal bacterial infection is caused by *Gardnerella vaginalis*, and *Atopobium vaginae*.

6. The method according to claim 1, wherein the vaginal bacterial infection is a recurrent vaginal bacterial infection.

7. The method according to claim 1, wherein furazidin is administered in the form of a tablet, capsule, cream, gel, lotion, foam, pessary, or globule.

8. The method according to claim 1, wherein the dose of furazidin is 1 mg to 10 mg.

9. The method according to claim 1, wherein 1 mg to 300 mg of furazidin is administered daily for ten days.

10. The method according to claim 9, wherein 1 mg to 10 mg of furazidin is administered daily for ten days.

11. The method according to claim 1, wherein furazidin is administered in a single dose.

12. The method according to claim 1, comprising vaginally administering 1 to 300 mg per nystatin day of furazidin in a single dose to the infected woman.

13. The method according to claim 1, comprising vaginally administering 1 mg to 10 mg per day of furazidin in a single dose to the infected woman.

14. The method according to claim 13, wherein the vaginal bacterial infection is caused by *Gardnerella vaginalis*.

15. The method according to claim 13, wherein the vaginal infection bacterial is caused by *Atopobium vaginae*.

16. The method according to claims 13, wherein the vaginal bacterial infection is a mixed type vaginal bacterial infection.

17. The method according to claim 16, wherein the mixed type vaginal bacterial infection is caused by *Gardnerella vaginalis* and *Atopobium vaginae*.

18. The method according to claim 13, wherein the vaginal bacterial infection is a recurrent vaginal bacterial infection.

19. The method according to claim 13, wherein furazidin is administered in the form of a tablet.

20. The method according to claim 1, comprising vaginally administering 1 mg to 10 mg per day of furazidin in a single dose in the form of a tablet.

\* \* \* \* \*